(12) United States Patent
Vuorenmaa et al.

(10) Patent No.: US 9,358,218 B2
(45) Date of Patent: Jun. 7, 2016

(54) USE OF SAPONIFIED TALL OIL FATTY ACID

(71) Applicant: Hankkija Oy, Hyvinkaa (FI)

(72) Inventors: Juhani Vuorenmaa, Hyvinkaa (FI); Hannele Kettunen, Tervakoski (FI)

(73) Assignee: Hankkija Oy, Hyvinkaa (FI)

( * ) Notice: Subject to any disclaimer, the term of this patent is extended or adjusted under 35 U.S.C. 154(b) by 0 days.

(21) Appl. No.: 14/401,253

(22) PCT Filed: May 14, 2013

(86) PCT No.: PCT/FI2013/050520
§ 371 (c)(1),
(2) Date: Nov. 14, 2014

(87) PCT Pub. No.: WO2013/182737
PCT Pub. Date: Dec. 12, 2013

(65) Prior Publication Data
US 2015/0148416 A1    May 28, 2015

(30) Foreign Application Priority Data
May 14, 2012 (FI) ...................................... 20125509

(51) Int. Cl.
| A61K 36/13 | (2006.01) |
| A61K 31/20 | (2006.01) |
| A61K 36/15 | (2006.01) |
| A23K 1/16 | (2006.01) |
| A23K 1/18 | (2006.01) |
| A61K 31/19 | (2006.01) |
| A23L 1/30 | (2006.01) |

(52) U.S. Cl.
CPC ................ *A61K 31/20* (2013.01); *A23K 1/164* (2013.01); *A23K 1/1813* (2013.01); *A23K 1/1826* (2013.01); *A23L 1/3008* (2013.01); *A61K 31/19* (2013.01); *A61K 36/13* (2013.01); *A61K 36/15* (2013.01); *A23V 2002/00* (2013.01); *Y02P 60/56* (2015.11)

(58) Field of Classification Search
CPC ....... A61K 36/13; A61K 31/20; A61K 36/15; A23K 1/07; A23K 1/813
See application file for complete search history.

(56) References Cited

U.S. PATENT DOCUMENTS

| 2,423,236 A | 7/1947 | Harwood et al. |
| 3,311,561 A * | 3/1967 | Campbell ............ C10M 173/00 252/75 |
| 5,460,648 A | 10/1995 | Walloch et al. |
| 6,020,377 A | 2/2000 | O'Quinn et al. |
| 6,229,031 B1 | 5/2001 | Strohmaier et al. |
| 2006/0286185 A1 | 12/2006 | Prokosch |
| 2011/0081442 A1 | 4/2011 | Weill et al. |
| 2011/0212218 A1 | 9/2011 | Herranen et al. |
| 2015/0164966 A1 * | 6/2015 | Vuorenmaa ............ A61K 36/13 424/195.18 |
| 2015/0238454 A1 * | 8/2015 | Vuorenmaa ............ A61K 31/20 514/558 |

FOREIGN PATENT DOCUMENTS

| CN | 101461443 A | 6/2009 | |
| GB | 955316 A | 4/1964 | |
| GB | 2 139 868 A | 11/1984 | |
| NL | WO 2008154522 A1 * | 12/2008 | ............... A23D 9/02 |
| WO | WO 0202106 A1 * | 1/2002 | ............. A23K 1/164 |

OTHER PUBLICATIONS

International Search Report for corresponding International Patent Application No. PCT/FI2013/050520 mailed Oct. 1, 2013.
Finnish Search Report for corresponding Finnish Patent Application No. 20125509 mailed Feb. 26, 2013.
Product Data Sheet SYLFAT® 2LTC tall oil fatty acid [online], Arizona Chemical, [last modified Jul. 20, 2009], retrieved Feb. 20, 2013, URL: http://www.arizonachemical.com/Global/PDS/EU_product_data_sheets/SYLFAT%C2%AE%202LTC.pdf.
Extended European Search Report for corresponding European Patent Application No. 13799838.1 mailed Nov. 13, 2015.
Smith, E. et al., "Isopimaric Acid from *Pinus nigra* shows Activity against Multidrug-resistant and EMRSA Strains of *Staphylococcus aureus*", *Phytotherapy Research*, 19(6): 538-542 (2005).
Savluchinske-Feio, S. et al., "Antimicrobial activity of resin acid derivatives", *Appl. Microbiol. Biotechnol.*, 72: 430-436 (2006).

* cited by examiner

*Primary Examiner* — Nyeemah A Grazier

(74) *Attorney, Agent, or Firm* — Merchant & Gould P.C.

(57) ABSTRACT

The present invention relates to use of a tall oil fatty acid which is modified by saponification in enhancing rumen fermentation and/or lowering rumen methane production.

6 Claims, 1 Drawing Sheet

USE OF SAPONIFIED TALL OIL FATTY ACID

This application is a National Stage Application of PCT/FI2013/050520, filed 14 May 2013, which claims benefit of Serial No. 20125509, filed 14 May 2012 in Finland and which applications are incorporated herein by reference. To the extent appropriate, a claim of priority is made to each of the above disclosed applications.

FIELD OF THE INVENTION

The invention relates to use of tall oil fatty acid which is modified by saponification.

BACKGROUND OF THE INVENTION

Imbalances in microbial populations and growth of harmful bacteria in the digestive tract of animals can cause significant losses in animal growth and production. These imbalances manifest themselves as intestinal disorders such as diarrhea. While microbial infections of animals have been prevented by the use of e.g. antibiotics and other agents that prevent the growth of microorganisms, stricter regulations on their use are expected. Ruminant animals can utilize fiber-rich raw materials which have little or no nutritional value for monogastrics like the human. However, the feed conversion efficiency of ruminants is relatively low and their methane production represents a remarkable share of the world's greenhouse gas emissions. With the increasing demand of food there is a need to improve the feed conversion efficiency of ruminants and to lower their methane production. Generally, there is an increasing demand for ingredients for use in animal feeding that can modulate the microbial population in the animal digestive tract but which are readily available, well tolerated and environmentally friendly.

Fractional distillation of crude tall oil, obtained as a by-product of the Kraft process of wood pulp manufacture, produces distilled tall oil (DTO) which typically comprises over 10% resin acids and less than 90% fatty acids. Further refinement of distilled tall oil produces tall oil fatty acid (TOFA), which is available in a variety of compositions differing in the fatty acids and resin acids content. Because TOFA is an inexpensive source of fatty acids, it has previously been used in animal nutrition as an energy source. For instance, GB 955316 discloses the use of alkali metal salts of tall oil fatty acids to improve weight gain and nitrogen retention in ruminant animals.

PURPOSE OF THE INVENTION

The purpose of the invention is to provide a new type of modified tall oil fatty acid/feed supplement for use in enhancing rumen fermentation and/or lowering rumen methane production.

The present inventors have surprisingly found that modification of TOFA improves the solubility of its components and resin acids in the digestive tract of an animal in particular and significantly increases its effectiveness in enhancing rumen fermentation and/or lowering rumen methane production.

SUMMARY

Use of a tall oil fatty acid which is modified by saponification according to the present invention is characterized by what is presented in claim 1.

DETAILED DESCRIPTION OF THE INVENTION

Figure 1A:
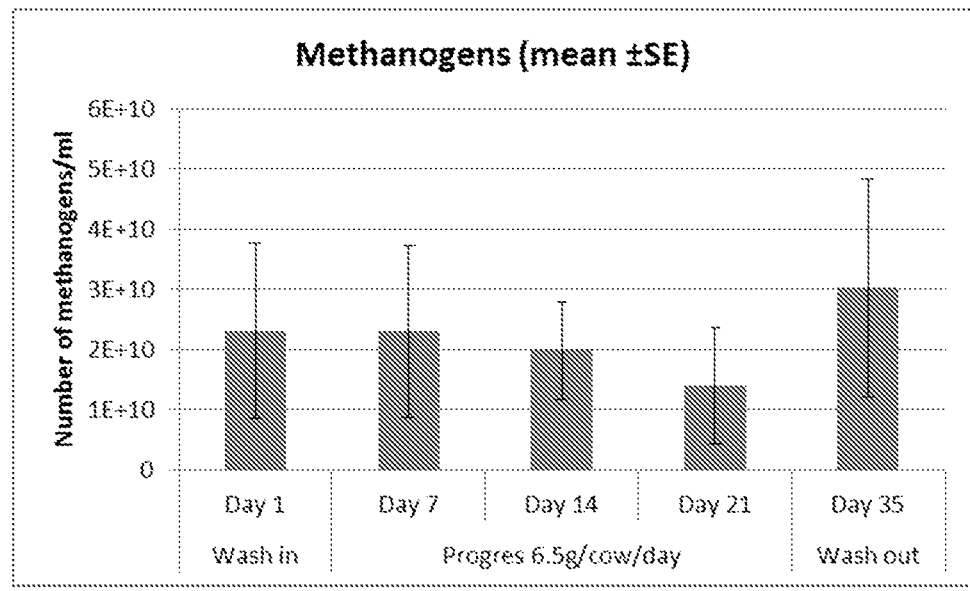

FIG. 1a The number of methane producing bacteria (number/ml) in the rumen fluid as a response to saponified TOFA.

Figure 1B:
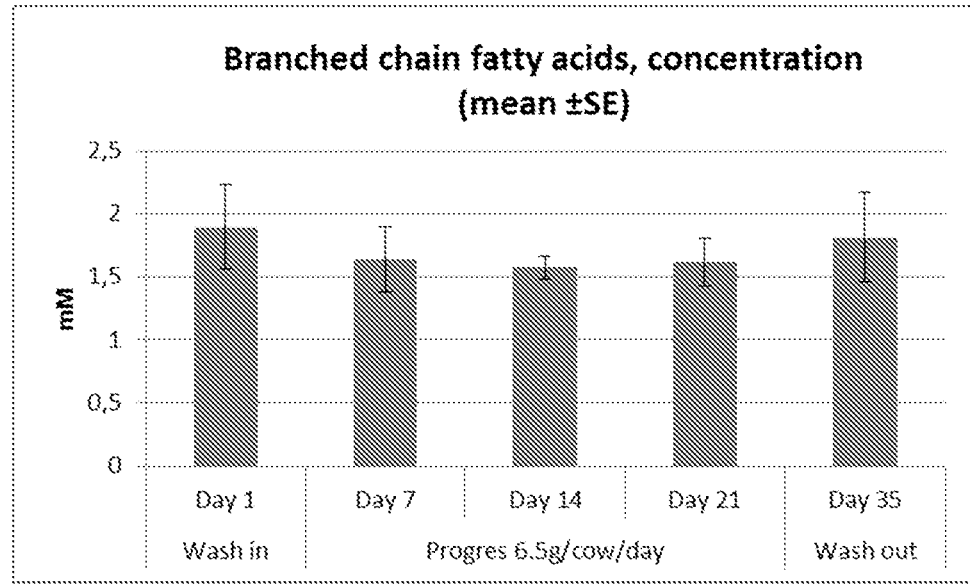

FIG. 1b Total concentration of branched chain fatty acids acid in the rumen fluid (mM) as a response to saponified TOFA.

The present invention is based on the realization that modified tall oil fatty acid can be used in enhancing rumen fermentation and/or lowering rumen methane production.

In fermentation fiber, especially cellulose and hemi-cellulose, is primarily broken down into the three volatile fatty acids (VFAs), acetic acid, propanoic acid and beta-hydroxy-butyric acid. Protein and non-structural carbohydrate (pectin, sugars, starches) are also fermented.

The term "tall oil fatty acid" or "TOFA" should be understood as referring to a composition obtained by distillation of crude tall oil and further refinement of distilled tall oil. TOFA or TOFA which is modified by saponification typically comprises 90-98% (w/w) fatty acids. Further, TOFA or TOFA which is modified by saponification may comprise 1-10% (w/w) resin acids.

Resin acids are known to have antimicrobial, including antibacterial, properties. However, the present inventors have found that resin acids of TOFA are poorly soluble in digestive juices and tend to precipitate in the digestive tract of an animal. Therefore their effectiveness in the digestive tract is less than optimal.

The modification of TOFA improves the solubility of its components and resin acids in the digestive tract of an animal.

In this context, the term "tall oil fatty acid which is modified by saponification" or "TOFA which is modified by saponification" should be understood as referring to TOFA that is chemically modified so as to improve the solubility of its components and resin acids in the digestive tract of an animal in particular.

In one embodiment of the present invention, the tall oil fatty acid which is modified by saponification comprises 1-10% (w/w) of resin acids.

In one embodiment of the present invention, TOFA or TOFA which is modified by saponification comprises 2-9% (w/w) resin acids.

In one embodiment of the present invention, TOFA or TOFA which is modified by saponification comprises 5-9% (w/w) resin acids.

In this context, the term "resin acids" should be understood as referring to a complex mixture of various acidic compounds comprised by tall oil which share the same basic skeleton including a three-fused ring. The exact composition of the resin acids present in TOFA varies e.g. according to the species of the trees the TOFA is obtained from and the processing conditions under which it is manufactured. Resin acids typically include compounds such as abietic acid, dehydroabietic acid, levopimaric acid, neoabietic acid, pimaric acid and isopimaric acid, only to mention a few.

In one embodiment of the present invention, TOFA or TOFA which is modified by saponification comprises 90-98% (w/w) of fatty acids.

Various processes for the saponification of TOFA using e.g. NaOH or CaOH are known to a person skilled in the art.

In one embodiment of the present invention, the TOFA which is modified by saponification, the TOFA soap, is dried. The modified TOFA can be dried by spray drying, drum drying or by any other known suitable drying method.

The present invention also relates to a feed supplement comprising the tall oil fatty acid which is modified by saponification and which is effective in enhancing rumen fermentation and/or lowering rumen methane production.

In one embodiment of the present invention, the feed supplement comprises a tall oil fatty acid which is modified by saponification and which comprises 1-10% (w/w) resin acids.

In one embodiment of the present invention, the feed supplement comprises a tall oil fatty acid which is modified by saponification and which comprises 2-9% (w/w) resin acids.

In one embodiment of the present invention, the feed supplement comprises a tall oil fatty acid which is modified by saponification comprises 5-9% (w/w) resin acids.

In this context, the term "feed supplement" should be understood as referring to a composition that may be added to a feed or used as such in the feeding of animals. The feed supplement may comprise different active ingredients. The feed supplement may be added in the feed in a concentration of 0.0001-5 kg/ton of dry weight, preferably 0.005-1 kg/ton, most preferably 0.01-0.1 kg/ton of the dry weight of the total amount of the feed. The modified TOFA or the feed supplement comprising the modified TOFA according to the invention may be added to the feed or feed supplement as such, or it may in general be further processed as desired.

Further, the TOFA which is modified by saponification or the feed supplement comprising the TOFA which is modified by saponification according to the invention may be added to the feed or feed supplement, or it may be administered to an animal separately (i.e. not as a part of any feed composition).

In this context, the term "feed composition" or "feed" should be understood as referring to the total feed composition of an animal diet or to a part thereof, including e.g. supplemental feed, premixes and other feed compositions. The feed may comprise different active ingredients.

In one embodiment of the present invention, the feed supplement comprises TOFA which is modified by saponification and which is absorbed into a carrier material suitable for the feed composition such as sugarbeet pulp.

In one embodiment of the present invention, the feed supplement comprises TOFA which is modified by saponification and which is dried.

The present invention also relates to a feed composition comprising the feed supplement according to the invention.

In one embodiment of the present invention, the feed composition comprises the feed supplement in an amount of 0.00001-0.5% (w/w), preferably 0.0005-0.1% (w/w), most preferably 0.001-0.01% (w/w) of the dry weight of the total amount of the feed.

In one embodiment of the present invention, the feed composition comprises the feed supplement in an amount of 0.0005-0.1% (w/w) of the dry weight of the total amount of the feed.

The modified tall oil fatty acid or feed supplement according to the invention is produced by saponification. The method comprises the steps of adding a base to an aqueous TOFA solution and heating the mixture. The mixture is stirred during the heating step. The mixture is heated at a temperature of 80-120° C., preferably at 85-95° C., for a period of 1-3 hours, preferably for 2 hours.

Any base suitable for saponification, such as an alkali metal hydroxide, can be used as the base. Normally, the base that is used is a sodium or potassium hydroxide.

In one embodiment of the present invention, the method of producing a modified tall oil fatty acid or feed supplement further comprises a step of drying. The dying can be carried out by spray drying, drum drying or by any other known drying method.

In this context, the term "harmful bacteria" should be understood as referring to any bacteria that is capable of affecting the digestive tract or health of an animal in an adverse manner, including competition for nutrients with the host animal. In this context, the term "microbial population" should be understood as referring to the microorganisms that inhabit the digestive tract, including the Bacteria and Archaea domains and microscopic members of the Eukaryote domain and also intestinal parasites. The microbial population will vary for different animal species depending on e.g. the health of an animal and on environmental factors.

In this context, the term "animal" should be understood as referring to all kinds of different ruminants. Non-limiting examples of different animals, including offspring, are cows, beef cattle, sheep and goats.

In one embodiment of the present invention, the TOFA which is modified by saponification is administered to an animal in an effective amount.

The present invention has a number of advantages. TOFA is a readily available, natural, low-cost and environmentally friendly material. Further, it is non-toxic and well tolerated. Subsequently, other benefits of the invention are e.g. lower costs per production unit and decreased environmental loads. The invention also allows the production of feed compositions and supplements at low cost.

The embodiments of the invention described hereinbefore may be used in any combination with each other. Several of the embodiments may be combined together to form a further embodiment of the invention. A product, a method or a use, to which the invention is related, may comprise at least one of the embodiments of the invention described hereinbefore.

EXAMPLES

In the following, the present invention will be described in more detail.

Example 1

Methane Inhibition Test

The saponified TOFA was manufactured by adding 140 mg of NaOH (sodium hydroxide) to 1 gram of TOFA, adding enough water to adjust the total dry matter (TOFA) percentage of the mixture to 18-20%, heating the mixture to +90° C., keeping the temperature at +90° C. for 120 minutes, during which time the mixture was gently stirred at 15 min intervals.

The methane inhibition test was conducted with rumen-fistulated dairy cows in order to study the potential of saponified TOFA to decrease the rate of methane production in the rumen. Rumen fluid samples were measured for the numbers of methanogenic bacteria, as they are the methane-producing organisms. The short chain fatty acid profiles, including the concentration of branched chain fatty acids, of the samples were measured as they indicate whether saponified TOFA had effects to ruminal fermentation.

Three rumen-fistulated, lactating dairy cows were given 6.5 g of dry saponified TOFA/head/day for 21 days, in four portions. TOFA soap was first dried onto sugar beet pulp and then mixed into the compound feed. Rumen samples were taken before the dietary intervention, once a week during the TOFA soap feeding, and after a two-week washout period. The fifteen samples of the trial were analysed for short chain fatty acids (SCFAs) by gas chromatography and numbers of methanogens, protozoa and total bacteria by qPCR.

Results

The results are illustrated in FIGS. 1a and 1b. The numbers of methane producing bacteria decreased numerically during the TOFA soap feeding period (FIG. 1a), while protozoa and the total number of bacteria were not affected by the product. The total concentration of SCFAs varied between 80 mM and 100 mM, without statistically significant differences between the sampling time points. The levels of lactic, propionic, and valeric acids and total short chain fatty acids tended to decrease in the rumen fluid during the TOFA feeding period. TOFA soap tended to increase the relative proportion of butyric acid. The concentration and relative proportion of branched chain fatty acids tended to decrease as a response to dietary TOFA soap amendment (FIG. 1b).

The experiment shows that the saponified TOFA lowers the amount of methanogens and thus lowers rumen methane production. The experiment also shows that the saponified TOFA enhances rumen fermentation.

It is obvious to a person skilled in the art that, with the advancement of technology, the basic idea of the invention may be implemented in various ways. The invention and its embodiments are thus not limited to the examples described above; instead they may vary within the scope of the claims.

The invention claimed is:

1. A method of enhancing rumen fermentation and/or lowering rumen methane production comprising:
   administering a saponified tall oil fatty acid to a ruminant.
2. The method according to claim 1, wherein the saponified tall oil fatty acid comprises 1-10% (w/w) resin acids.
3. The method according to claim 1, wherein the saponified tall oil fatty acid comprises 2-9% (w/w) resin acids.
4. The method according to claim 1, wherein the saponified tall oil fatty acid comprises 5-9% (w/w) resin acids.
5. The method according to claim 1, wherein the saponified tall oil fatty acid comprises 91-98% (w/w) fatty acids.
6. The method according to claim 1, wherein the saponified tall oil fatty acid is dried.

* * * * *